United States Patent [19]

Hubert et al.

[11] Patent Number: 4,937,849
[45] Date of Patent: Jun. 26, 1990

[54] X-RADIATION GATING AND TARGET DEVICE

[75] Inventors: Guenter Hubert, Baiersdorf; Johann Finkenzeller, Erlangen, both of Fed. Rep. of Germany

[73] Assignee: Siemens Aktiengesellschaft, Berlin and Munich, Fed. Rep. of Germany

[21] Appl. No.: 205,363

[22] Filed: Jun. 10, 1988

[30] Foreign Application Priority Data

Jun. 15, 1987 [DE] Fed. Rep. of Germany ... 8708397[U]

[51] Int. Cl.$^5$ .............................................. G21K 1/00
[52] U.S. Cl. ..................................... 378/155; 378/181; 378/154; 378/150
[58] Field of Search ............... 378/145, 147, 150, 154, 378/155, 167, 172, 175, 181

[56] References Cited

U.S. PATENT DOCUMENTS

| | | | |
|---|---|---|---|
| 2,591,536 | 4/1952 | Gieringer et al. | 378/155 |
| 2,767,323 | 10/1956 | Stava et al. | 378/155 |
| 3,665,186 | 5/1972 | Tajima | 378/154 |
| 4,105,920 | 8/1978 | Pury et al. | 378/155 |
| 4,132,897 | 1/1979 | Ohlson et al. | 378/154 |
| 4,380,819 | 4/1983 | Everett et al. | 378/175 |
| 4,476,569 | 10/1984 | Ogo | 378/147 |
| 4,542,521 | 9/1985 | Hahn et al. | 378/154 |
| 4,577,341 | 3/1986 | Schwieker et al. | 378/150 |
| 4,706,269 | 11/1987 | Reina et al. | 378/154 |

FOREIGN PATENT DOCUMENTS

| | | |
|---|---|---|
| 2842659 | 4/1980 | Fed. Rep. of Germany . |
| 2921034 | 11/1980 | Fed. Rep. of Germany ...... 378/154 |
| 3034915 | 4/1982 | Fed. Rep. of Germany . |
| 3331555 | 4/1985 | Fed. Rep. of Germany . |
| 3610080 | 10/1986 | Fed. Rep. of Germany . |
| 0830442 | 7/1938 | France ................................ 378/155 |

Primary Examiner—Craig E. Church
Assistant Examiner—John C. Freeman
Attorney, Agent, or Firm—Hill, Van Santen, Steadman & Simpson

[57] ABSTRACT

A gating and target device for an x-ray examination apparatus has a secondary radiation diaphragm and an x-ray film cassette, the secondary radiation diaphragm having two diaphragm plates disposed in parallel planes, and moveable relative to each other so that the diaphragm plates can be adjusted to at least partially overlap. Each of the diaphragm plates has a diaphragm opening therein, with the remainder of the plate being impermeable to x-radiation, so that by adjusting the relative positions of the plates, an opening of selected size may be formed by either one of said diaphragm plates at least partially covering the opening of the other diaphragm plate. To minimize the thickness of the device, and thus to minimize the distance between the target x-ray film and an examination subject, one of the diaphragm plates has a scattered ray grid structurally integrated within the opening of that plate.

12 Claims, 2 Drawing Sheets

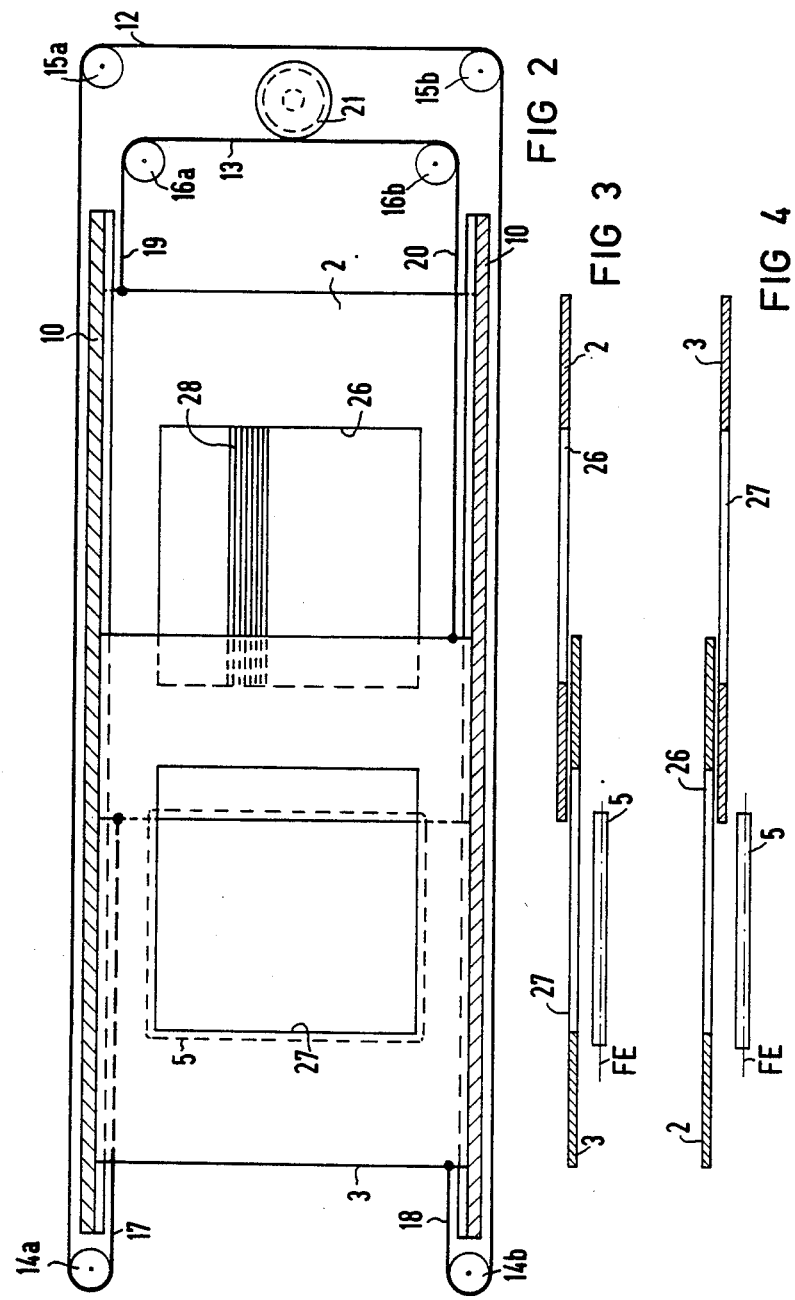

X-RADIATION GATING AND TARGET DEVICE

BACKGROUND OF THE INVENTION

1. Field of the Invention

The present invention is directed to a gating and target device, herein also referred to as spot film device, for use in an x-ray examination apparatus, and in particular to such a device including a secondary radiation diaphragm comprising two moveable diaphragm plates, a scattered ray grid, and an x-ray film cassette holder.

2. Description of the Prior Art

Spot film devices which also include a holder for an xray film cassette and a scattered ray grid are known in the art as described, for example, in German OS No. 28 42 659. This device includes a secondary radiation diaphragm consisting of two diaphragm plates and a means for moving the diaphragm plates in respective parallel planes toward and away from each other to adjust the size of the opening formed by the combination of the respective opening limited by the diaphragm plates. The scattered ray grid in this device is disposed in a plane parallel to the respective planes in which the diaphragm plates are disposed, so that the diaphragm plates and the scattered ray grid occupy successive planes between a wall of the device against which the examination subject lies, and the x-ray film cassette holder. Thus a relatively large distance exists between an examination subject, of whom an image is to be obtained, and the plane in which the film of the x-ray film cassette is disposed. This large distance has a disadvantageous effect on the quality of the x-ray exposure of the examination subject because, as is known, unsharpness of the exposure increases with increasing distance between the subject and the film plane.

SUMMARY OF THE INVENTION

It is an object of the present invention to provide a spot film device for use in an x-ray examination apparatus having a secondary radiation diaphragm, a scattered ray grid, and an xray film cassette holder wherein the distance between the examination subject and the film plane is as small as possible, thereby minimizing the unsharpness of the x-ray image.

The above object is achieved in accordance with the principles of the present invention in a spot film device having two moveable diaphragm plates, each having a diaphragm opening therein, a scattered ray grid structurally integrated within the diaphragm opening of one diaphragm plate, and means for moving the diaphragm plates relative to each other and past one another such that either diaphragm plate may be positioned with its diaphragm opening in front of an x-ray film cassette holder and the diaphragm opening positioned in front of the x-ray film cassette holder may at least partially be covered by the other diaphragm plate. Depending on the extent to which an x-ray film cassette contained in the holder is exposed by the diaphragm opening on the one hand and the amount to which the other diaphragm plate covers the diaphragm opening on the other hand, exposures of different formats may be taken.

Depending on whether the means for moving the diaphragm plates are activated such that the diaphragm plate whose diaphragm opening contains the scattered ray grid or the diaphragm plate whose diaphragm opening is fashioned without a scattered ray grid is disposed with its respective diaphragm opening in front of the x-ray film cassette, exposures with or without scattered ray grid may be taken.

Because the space reserved in conventional devices for the scattered ray grid is not needed in the device disclosed herein, a smaller distance exists between the wall of the device against which the examination subject lies and the film plane.

In one embodiment of the invention, the adjustment mechanism for the diaphragm plates is disposed in the same plane as the diaphragm plates. In this embodiment the space occupied by the adjustment mechanism therefore does not add to the distance between the examination subject and the film plane.

The distance between the examination subject and the film plate can be further reduced in an embodiment of the invention wherein the diaphragm plates have respective surfaces sliding directly on each other. In this embodiment, one of the diaphragm plates may have a low-friction coating on is sliding surface, facing the other diaphragm plate, to maintain the actuating forces as low as possible. To provide adequate guidance for the diaphragm plates, the plates may be disposed in U-shaped guide rails or channels extending along the direction of movement of the diaphragm plates on both sides of the diaphragm plates. The U-shaped guide rails have parallel legs and a connecting leg connecting said parallel legs extending transversely relative to the direction of movement of the plates. The respective parallel legs are disposed with the diaphragm plates therebetween and the connecting legs guide the diaphragm plates transversely relative to the direction of movement.

In an embodiment for applications wherein it is inadvisable to allow the diaphragm plates to slide directly on each other, the guide rails may have a T-shaped cross section, with a center leg extending between the diaphragm plates and outer legs or flanges guiding the outside edges of the diaphragm plates. All of the legs or flanges extend transversely relative to the direction of movement of the plates. Canting of the diaphragm plates within the guide rails can be avoided in an embodiment wherein the diaphragm plates have a length along the direction of their movement which at least corresponds to the width of the plates in a direction transverse to the direction of movement.

The adjustment mechanism for the diaphragm plates includes two traction elements having opposite ends respectively attached to different diaphragm plates, and guided around deflecting rollers so that the sections of each traction element which are attached to different diaphragm plates proceed parallel to each other, and the sections of the traction elements attached to the each respective diaphragm plate extend in opposite directions. One of the traction elements can be driven. An adjustment mechanism of this type permits the synchronous adjustment of the diaphragm plates, and permits the adjustment mechanism to be disposed next to the diaphragm plates within a space defined by the combined thicknesses of the two diaphragm plates—following "plates", so that the adjustment mechanism does not add to the distance between the examination subject and the film plane.

The scattered ray grid may consist of strip-shaped lamellae which proceed parallel to the direction of movement of the diaphragm plates. If the device disclosed herein is used in combination with an x-ray tube in a system having a fixed distant between the x-ray tube and the scattered ray grid, the use of lamellae proceeding parallel to the direction of movement of the diaphragm plates to form the scattered ray grid ensures that the grid will be permanently focused with respect to the focus of the x-ray beam. This would not be possible in the case of, for example, lamellae proceeding transversely relative to the direction of movement of the plates.

The device may further include a partition consisting of low-friction material disposed between the rear diaphragm plate, i.e., the diaphragm plate farther from the x-ray source, and the receptacle for the x-ray film cassette, the partition assisting in guiding the x-ray film cassette within the receptacle.

DESCRIPTION OF THE DRAWINGS

FIG. 2 is a plane view, partly in section, of the device of FIG. 1.

FIGS. 3 and 4 are side view schematically showing different operating positions for the diaphragm plates in the device of FIGS. 1 and 2.

DESCRIPTION OF THE PREFERRED EMBODIMENTS

Figure 1:
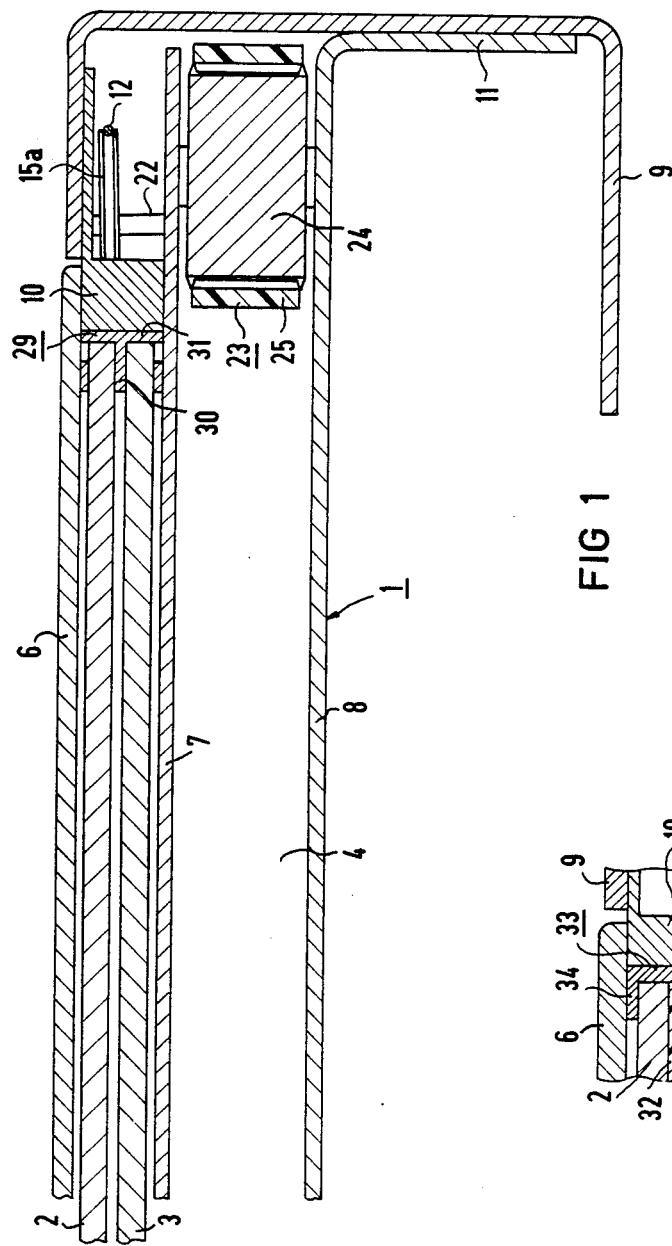
FIG. 1 is a side sectional view of a portion of an x-radiation gating and target device constructed in accordance with the principles of the present invention.

An x-radiation gating and target device is shown in two views in FIGS. 1 and 2. The device includes a housing, generally referenced at 1, in which a secondary radiation diaphragm consisting of two diaphragm plates 2 and 3 is disposed. The plates 2 and 3 consist of material impermeable to x-radiation. The housing also includes a cassette receptacle 4 into which an x-ray film cassette 5 (not shown in FIG. 1 and indicated with dashed lines in FIG. 2) can be introduced. The housing 1 has a wall 6 against which an examination subject rests during the production of an x-ray exposure, a partition 7, and a wall 8. At least the wall 6 and the partition 7 consist of material transmissive for x-radiation.

The diaphragm plates 2 and 3 are disposed between the wall 6 and the partition 7, with the partition 7 and the wall 8 limiting the cassette receptacle 4.

The housing 1 also includes a frame 9, by which the x-ray gating and target device can be attached to an x-ray examination apparatus with which it is to be used.

Two spacers 10 are provided at each side of the diaphragm plates 2 and 3, extending in the direction of movement of the plates. The spacers 10 support the wall 6 and the partition 7, and are attached to the frame 9. The wall is attached to the frame 9 by an angled flange 11.

In FIG. 2, the elements of the housing 1 have been omitted for clarity. As can be seen in FIG. 1, the diaphragm plates 2 and 3 are disposed in planes parallel to each other and are provided with an adjustment mechanism. The adjustment mechanism shown in FIG. 2 includes two traction elements, in the form of cables 12 and 13. The cables 12 and 13 each have one end attached to the diaphragm plate 2, and an opposite end attached to the diaphragm plate 3. The cable 12 is guided via deflection rollers 14a, 14b, 15a and 15b, and the cable 13 is guided via deflection rollers 16a and 16b. The cable 12 has sections 17 and 18, respectively attached to the different diaphragm plates 2 and 3, which proceed parallel to each other, and the cable 13 has similar sections 19 and 20, which also proceed parallel to each other, with all of the sections 17, 18, 19 and 20 proceeding parallel to each other in the embodiment of FIG. 2. Moreover, the cables 12 and 13 are guided around their respective deflection rollers so that the respective sections 17 and 19 of the cables 12 and 13 attached to the diaphragm plate 2 extend in opposite directions starting from plate 2, and the sections 18 and 20 of the respective cables 12 and 13 attached to the diaphragm plate 3 extend in opposite directions starting from plate 3. The cable 13 is looped around a motor-driven drive roller 21.

The diaphragm plates 2 and 3 can thus be synchronously adjusted relative to each other and past one another (see FIGS. 3 and 4) by rotating the drive roller 21 clockwise or counter clockwise. Because the cables 12 and 13 each have one end attached to the diaphragm plate 2 and each have an opposite end attached to the diaphragm plate 3, and because the diaphragm plate 2 and 3 are disposed in different planes, the rotational axes of the deflecting rollers 14a through 16b are inclined by a slight amount as is needed for free running of the cables 12 and 13. This is shown in FIG. 1 with respect to the deflection roller 15a, which is mounted on an axle 22 having a rotational axis slightly deviating from the vertical. As can also be seen in FIG. 1, the entire adjustment mechanism is located in a common plane with the diaphragm plates 2 and 3.

A motor driven conveyor is provided for introducing an x-ray film cassette 5 into the cassette receptacle 4. This conveyor includes a toothed belt 23 guided around two pulleys disposed laterally within the cassette receptacle 4. One of the pulleys is motor-driven, and only the other pulley 24 is visible in FIG. 1. The toothed belt has a lower side 25, facing toward the cassette receptacle 4, which proceeds parallel to the direction of movement of the x-ray film cassette 5. Slide rollers (not shown in FIG. 1) are provided at the side of the cassette receptacle 4 opposite the side 25 of the toothed belt 23, with the x-ray film cassette 5 being inserted in the receptacle 4 between the slide rollers and the toothed belt 23. When an x-ray film cassette 5 is introduced into the receptacle 4, a drive motor (not shown) for the toothed belt 23 is activated, for example, by a light barrier actuated by the x-ray film cassette 5. This causes the toothed belt 23 to draw the cassette 5 into the receptacle 4. After an x-ray exposure has been completed, the x-ray film cassette 5 is conveyed out of the receptacle 4 under motor drive.

As can be seen in FIG. 2, each of the diaphragm plates 2 and 3 has a respective diaphragm opening 26 and 27. As used herein, "diaphragm" and "diaphragm plate" and "diaphragm opening" refer to a structure disposed in the path of the x-ray beam which interacts with the beam to block a peripheral portion thereof and thereby to limit or define the size of the beam. The diaphragm opening 26 of the diaphragm plate 2 is provided with a structurally integrated scattered ray grid 28. The scattered ray grid 28 consists of a plurality of lamellae (of which only a few are shown in FIG. 2) which extend in the direction of movement of the diaphragm plates 2 and 3. Using the adjustment mechanism described above, which permits the diaphragm plates 2 and 3 to be moved relative to and past one another, it is possible as shown in FIGS. 3 and 4 to selectively position the diaphragm opening 26, or the diaphragm opening 27, in front of the x-ray film cassette 5. This permits an x-ray exposure to be optionally produced with or without the presence of the scattered ray grid 28 in the beam. As a consequence of the synchronous adjustability of the diaphragm plates 2 and 3 relative to each other, it is also possible to at least partially cover either the diaphragm opening 26 of the diaphragm plate 2 with a portion of the diaphragm plate 3, or the diaphragm opening 27 of the diaphragm plate 3 with a portion of the diaphragm plate 2. This permits the size of either the diaphragm opening 26 or the diaphragm opening 27 to be selectively adjusted to a particular exposure format.

As a result of the structure described above, the distance between the wall 6 of the housing 1 and the cassette receptacle 4, i.e., the film plane, is very small in comparison to conventional devices, because a separate plane for the scattered ray grid 28 is eliminated, and the diaphragm plates 2 and 3 are disposed only a slight distance from each other. The distance between an examination subject and the film plane FE, shown in FIGS. 3 and 4, is thus significantly reduced, so that x-ray exposures with decreased blurring or unsharpness can be achieved.

As shown in FIG. 1, the diaphragm plates 2 and 3 are guided in a guide rail 29, attached to the spacer 10. The guide rail 29 has a T-shaped cross section, with a center leg 30 disposed between the plates 2 and 3, and side flanges 31 guiding the plates 2 and 3 transversely relative to their direction of movement. The diaphragm plates 2 and 3 have a length in the direction of movement which is at least equal to their width transversely to the direction of movement, so that free running guidance of the diaphragm plates 2 and 3 is insured. The wall 6 and the partition 7 also assist in guiding the plates 2 and 3 in a direction perpendicular to the direction of movement of the plates. The partition 7 may consist of low-friction material, and simultaneously functions as a guide for the x-ray film cassette 5.

Figure 5:
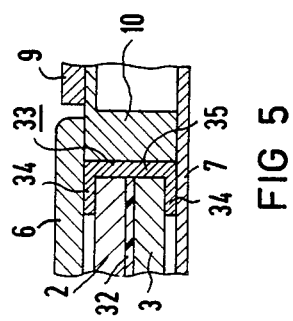
FIG. 5 is a side sectional detail of one embodiment for guiding the diaphragm plates in accordance with the principles of the present invention.

Another embodiment of a guide rail is shown in FIG. 5. In this embodiment, the plates 2 and 3 have respective surfaces facing each other which directly slide on each other. One of the plates, such as the diaphragm plate 2, may be provided with a low-friction coating on the surface thereof facing the diaphragm plate 3 to reduce the frictional resistance which opposes sliding movement of the diaphragm plates 2 and 3. In this embodiment, a U-shaped guide rail 33 is attached to each of the spacers 10. The guide rail 33 has spaced parallel legs 34 surrounding the edges of the outside surfaces of the plates 2 and 3, and thus guiding the plates 2 and 3 in combination with a connecting leg 35 which provides for guidance transversely to the direction of movement.

The above-described embodiment of the adjustment mechanism for the diaphragm plates 2 and 3 can be varied to satisfy different requirements without departing from the inventive concept disclosed herein. For example, it is not necessary in some instances that the diaphragm plates 2 and 3 be synchronously adjustable relative to each other. In accordance with the principles of the present invention, it is sufficient that one of the diaphragm plates have a scattered ray grid 28 within its diaphragm opening, and that the plates be moveable, in an manner, so as to at least partially overlap.

Although modifications and changes may be suggested by those skilled in the art it is the intention of the inventors to embody within the patent warranted hereon all changes and modifications as reasonably and properly come within the scope of their contribution to the art.

We claim as our invention:

1. A spot film device for an apparatus for conducting an x-ray examination of a subject, said apparatus being for use with an x-ray film cassette, said device comprising:
   a housing, said housing having a wall;
   a receptacle means in said housing for receiving an x-ray film cassette on which an x-ray image of said subject is to be recorded with said wall disposed between said subject and said x-ray film cassette;
   a secondary radiation diaphragm disposed between said wall of said housing and said x-ray film cassette receptacle, said secondary radiation diaphragm consisting of two diaphragm plates moveable in parallel planes, each diaphragm plate having a diaphragm opening therein, and only one of said diaphragm plates having a scattered ray grid integrally formed with the diaphragm opening thereof; and
   means for moving said diaphragm plates relative to each other and past one another in said parallel planes in front of said x-ray film cassette receptacle such that either one of said diaphragm plates may be positioned with its respective diaphragm opening in front of an x-ray film cassette disposed in said receptacle and said respective diaphragm opening may be at least partially be overlapped by the other diaphragm plate.

2. A device as claimed in claim 1, wherein one of said diaphragm plates has a surface closest to said wall of said housing and the other of said diaphragm plates has a surface farthest from said wall of said housing, said surfaces defining a space therebetween, and wherein said means for moving is disposed next to said secondary diaphragm within said space.

3. A device as claimed in claim 1, wherein each of said diaphragm plates has a surface, said diaphragm plates being disposed with said surfaces facing each other and sliding directly on each other.

4. A device as claimed in claim 3, further comprising a low-friction coating covering the surface of one of said diaphragm plates.

5. A device as claimed in claim 3, further comprising a pair of U-shaped guide rails extending on opposite sides of said diaphragm plates in the direction of movement of said diaphragm plates, each guide rail having spaced parallel legs and a connecting leg connecting said parallel legs, all legs extending transversely relative to said direction of movement, said parallel legs being disposed with said diaphragm plates therebetween and said connecting legs guiding said diaphragm plates transversely relative to said direction of movement.

6. A device as claimed in the claim 5, wherein each of said diaphragm plates has a length in the direction of movement thereof, and a width extending transversely relative to said direction of movement which is at least equal to said length.

7. A device as claimed in claim 1, further comprising a pair of T-shaped guide rails extending on opposite sides of said diaphragm plates in the direction of movement of said diaphragm plates, said guide rails each having a central leg extending between said diaphragm plates and side flanges disposed against said diaphragm plates for guiding said diaphragm plates transversely relative to said direction of movement.

8. A device as claimed in the claim 7, wherein each of said diaphragm plates has a length in the direction of movement thereof, and a width extending transversely relative to said direction of movement which is at least equal to said length.

9. A device as claimed in claim 1, wherein said means for moving comprises:
two traction elements each having one end attached to one of said diaphragm plates and an opposite end attached to the other of said diaphragm plates;
a plurality of deflection rollers disposed for guiding said traction elements such that each traction element has a section attached to one diaphragm plate and another section attached to the other diaphragm plate said sections being disposed parallel to each other with the sections attached to each respective diaphragm plate extending in opposite directions starting from said respective diaphragm plate; and
means for driving at least one of said traction elements.

10. A device as claimed in claim 1, wherein said scattered ray grid consists of a plurality of strip-shaped lamellae extending parallel to the direction of movement of said diaphragm plates.

11. A device as claimed in claim 1, further comprising a partition consisting of low-friction material disposed between said secondary radiation diaphragm and said receptacle.

12. A spot film device for an x-ray examination apparatus comprising a secondary radiation diaphragm consisting of a pair of diaphragm plates each having a diaphragm opening therein and disposed in parallel planes, means for moving said diaphragm plates in said respective parallel planes to selected positions in a range of positions from non-overlapping to one diaphragm plate at least partially overlapping the diaphragm plate, and a scattered ray grid structurally integrally formed in the opening of one of said diaphragm plates.

* * * * *